US010406310B2

(12) United States Patent
Fromentin (10) Patent No.: US 10,406,310 B2
(45) Date of Patent: Sep. 10, 2019

(54) BREATHING ASSISTANCE SYSTEM WITH SPEECH DETECTION

(71) Applicant: RESMED PARIS SAS, Moissy, Cramayal (FR)

(72) Inventor: Cyril Fromentin, Cramayal (FR)

(73) Assignee: RESMED PARIS SAS, Moissy-Cramayel (FR)

( * ) Notice: Subject to any disclaimer, the term of this patent is extended or adjusted under 35 U.S.C. 154(b) by 782 days.

(21) Appl. No.: 14/422,971

(22) PCT Filed: Aug. 22, 2013

(86) PCT No.: PCT/EP2013/067474
§ 371 (c)(1),
(2) Date: Feb. 20, 2015

(87) PCT Pub. No.: WO2014/029849
PCT Pub. Date: Feb. 27, 2014

(65) Prior Publication Data
US 2015/0202395 A1 Jul. 23, 2015

(30) Foreign Application Priority Data
Aug. 22, 2012 (AU) ................................ 2012903613

(51) Int. Cl.
*A61M 16/04* (2006.01)
*A61M 16/00* (2006.01)
(Continued)

(52) U.S. Cl.
CPC .... *A61M 16/0468* (2013.01); *A61M 16/0006* (2014.02); *A61M 16/021* (2017.08);
(Continued)

(58) Field of Classification Search
CPC ..... A61M 16/00–0012; A61M 16/0051–0084; A61M 16/0096;
(Continued)

(56) References Cited

U.S. PATENT DOCUMENTS 5,626,132 A   5/1997  Miller et al.
6,532,959 B1  3/2003  Berthon-Jones
(Continued)

FOREIGN PATENT DOCUMENTS

CN   2039960 U   6/1989
CN   2519567 Y   10/2002
(Continued)

OTHER PUBLICATIONS

International Search Report for PCT/EP2013/067474, dated Dec. 13, 2013, 6 pages.
(Continued)

*Primary Examiner* — Tan-Uyen T Ho
*Assistant Examiner* — Ned T Heffner
(74) *Attorney, Agent, or Firm* — Nixon & Vanderhye P.C.

(57) ABSTRACT

Disclosed is a breathing assistance system (10) comprising: a ventilator (12), a breathing lumen (14) arranged to communicate a flow of air between the ventilator and a tracheostomy tube (16) in the trachea of a patient, and a sensor (24) configured to generate a vibration signal representing vocal cord vibrations of the patient. The system is configured to facilitate the flow of exhaled air to the atmosphere via the upper airway of the patient in response to detection in the vibration signal of speech or attempted speech by the patient.

38 Claims, 7 Drawing Sheets

(51) Int. Cl.
*A61M 16/10* (2006.01)
*A61M 16/20* (2006.01)

(52) U.S. Cl.
CPC .......... *A61M 16/105* (2013.01); *A61M 16/20* (2013.01); *A61M 16/107* (2014.02); *A61M 2205/07* (2013.01); *A61M 2205/3334* (2013.01); *A61M 2205/3375* (2013.01); *A61M 2205/35* (2013.01); *A61M 2205/75* (2013.01)

(58) Field of Classification Search
CPC ......... A61M 16/04–0402; A61M 16/06–0661; A61M 2016/0015–0042; A61M 2016/0413; A61M 16/16–168; A61M 16/08; A61M 16/0413; A61M 2230/00; A61M 2230/005; A61M 2230/202–205; A61M 2230/40–46; A61M 16/22; G05B 2/00; G05B 2/202; A61B 5/082–097
See application file for complete search history.

(56) References Cited

U.S. PATENT DOCUMENTS

| | | | |
|---|---|---|---|
| 2004/0016433 | A1 | 1/2004 | Estes et al. |
| 2005/0126578 | A1 | 6/2005 | Garrison et al. |
| 2005/0235993 | A1 | 10/2005 | Baecke et al. |
| 2007/0144516 | A1* | 6/2007 | Doyle ............... A61M 16/0883 128/204.18 |
| 2008/0060646 | A1 | 3/2008 | Isaza |
| 2008/0060656 | A1* | 3/2008 | Isaza ................ A61M 16/0468 128/207.16 |
| 2009/0205662 | A1* | 8/2009 | Kwok ............... A61M 16/0051 128/204.23 |
| 2011/0175728 | A1 | 7/2011 | Baker |
| 2012/0055471 | A1* | 3/2012 | Hadas ............... A61M 16/0816 128/201.19 |
| 2012/0145156 | A1 | 6/2012 | Lofaso et al. |

FOREIGN PATENT DOCUMENTS

| | | |
|---|---|---|
| CN | 1443349 A | 9/2003 |
| DE | 197 50 536 | 5/1999 |
| FR | 2 945 217 A1 | 11/2010 |
| JP | 61-232842 | 10/1986 |
| JP | 2001-86583 A | 3/2001 |
| JP | 2001-245984 | 9/2001 |
| JP | 2008-543383 A | 12/2008 |
| JP | 2008-546432 A | 12/2008 |
| JP | 2010-502401 A | 1/2010 |
| JP | 2011-529709 A | 12/2011 |
| WO | WO 2006/133493 | 12/2006 |
| WO | WO 2006/133495 A1 | 12/2006 |
| WO | WO 2008/033730 A2 | 3/2008 |
| WO | WO 2008/146264 A2 | 12/2008 |
| WO | 2011/047207 | 4/2011 |

OTHER PUBLICATIONS

Response to Written Opinion for PCT/EP2013/067474, dated Jun. 23, 2014, 16 pages.
International Preliminary Report on Patentability, 7 pages.
Chinese Office Action dated Mar. 4, 2016 in Chinese Application No. 201380053619.2, with English Translation (32 pages).
First Patent Examination dated Nov. 1, 2015 issued in Australian Application No. 2013304950 (3 pages).
Communication Pursuant to Article 94(3) EPC dated Jul. 21, 2017 in European Application No. 13 766 233.4 (6 pages).
First Examination Report dated Jun. 15, 2018 in New Zealand Application No. 734992 (4 pages).
Notification of Reason(s) for Refusal dated Apr. 26, 2016 in Japanese Application No. 2015-527923, with English Translation (10 pages).
Decision of Refusal dated Dec. 20, 2016 in Japanese Application No. 2015-527923, with English translation (4 pages).
Pre-Appeal Examination Report dated Aug. 9, 2017 in Japanese Application No. 2015-527923, with English translation (4 pages).
Notice of Cancellation of Pre-Examination dated Aug. 22, 2017 in Japanese Application No. 2015-527923 (Appeal No. 2017-005722), with English translation (3 pages).
Notification of Reason(s) for Refusal dated Apr. 3, 2018 in Japanese Application No. 2017-083874, with English translation (9 pages).
English translation of Notification of Reasons for Rejection for Japanese Application No. 2017-083874, dated Nov. 27, 2018, four pages.

* cited by examiner

BREATHING ASSISTANCE SYSTEM WITH SPEECH DETECTION

CROSS-REFERENCE TO RELATED APPLICATIONS

This application is the U.S. national phase of International Application No. PCT/EP2013/067474, filed on 22 Aug. 2013 which designated the U.S. and claims the benefit of Australian provisional application no. 2012903613, filed on 22 Aug. 2012, the disclosure of each of which are incorporated herein in its entirety by reference.

BACKGROUND OF THE INVENTION

Field of the Invention

The present technology relates to one or more of the diagnosis, treatment and amelioration of respiratory disorders. In particular, the present technology relates to medical devices, and their use for treating respiratory disorders.

Description of the Related Art

Respiratory Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the Essentials.

A range of respiratory disorders exist.

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Therapy

Ventilation has been used to treat CSR, OHS, COPD, MD and Chest Wall disorders.

PAP Devices

The air at positive pressure for ventilation is typically supplied to the airway of a patient by a PAP device or ventilator such as a motor-driven blower. The outlet of the blower is connected via a flexible delivery conduit to the airway of the patient.

Tracheostomy

Tracheostomy is a surgical procedure in which an incision on the anterior of the neck is made in order to open an airway into the trachea of a patient. Through the resulting opening a tracheostomy tube is inserted into the patient's trachea in order to allow him to breathe without the use of his upper airways.

A PAP device or ventilator used with such a tracheostomy tube can assist a patient by providing him with pressurised air or other breathable gas via the tube when the patient inhales, and by allowing exhaled air to be evacuated via the tube when the patient exhales.

One known ventilator suitable for tracheostomy patients is the Elisée, manufactured by ResMed.

Speech Difficulty

While connected to a valved ventilator, e.g. under uncuffed tracheostomy, the patient may attempt to speak. The normal operation of the ventilator will impair the quality of that speech by allowing the exhaled air to pass through the tracheostomy tube instead of through the upper airway, where the vocal cords are located.

Air being exhaled via a tracheostomy tube can impair speech from a patient under ventilation as the exhaled air is diverted from flowing through the patient's upper airway and along his vocal cords. To enable speech, a pressure below the vocal cords (between the lung and the vocal cords) above a minimum value of approximately 3 hPa is normally required. This is typically done in a non-tracheostomised person by contracting the vocal cords while there is air inside the lungs (after an inhalation). The pressure will then be the result of the normal exhalation of air through the vocal cords and then the mouth. On a tracheostomised patient, however, most of the exhaled air is not routed through the upper airway as the tracheostomy tube is located below the vocal cords, and it is easier for the air to pass through the exhalation valve of the breathing assistance system than through the upper airway.

According to an existing solution, the usual value of PEEP (Positive End-Expiratory Pressure) is increased by the PAP device so that the majority of exhaled air is redirected along the upper airway. According to another solution, a non-return valve, such as a Passy-Muir valve, is positioned along the conduit so that the only possible route for the exhaled air is via the upper airway.

French patent application no. FR 2945217 relates to a breathing assistance device for a tracheostomy patient that is said to facilitate breathing and speech of the patient. The assembly has an expiration circuit with an outlet opening for passage of the air exhaled by the patient, and a valve for opening/closing the outlet opening. When the patient inhales, the valve closes the outlet opening and when the patient exhales the valve opens the outlet opening. The device is also provided with means for positive control to be actuated by the patient for selectively moving the valve into the closed position when the patient exhales, so that the exhalation is via the upper airway, i.e., when he wishes to speak, or to a state where exhalation is done via the tracheostomy tube, i.e., when he does not wish to speak.

Most of the known solutions are permanent, i.e. they are kept constant throughout the therapy. Although allowing the patient to speak, they run counter to the whole purpose of tracheostomy. Only the device according to FR 2945217 is not permanent in that it provides a patient button to be activated by the patient. This activation thus requests a conscious act from the patient and also an ability to do so. This is problematic since the patient category that would benefit from such a feature (such as neuromuscular patients) often has a very limited ability to do so.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

The present technology particularly relates to a breathing assistance system and method that detects that a tracheostomised patient undergoing ventilation is speaking or attempting to speak, in response to which the breathing assistance system modifies its behaviour in order to facilitate or improve the quality of the patient's speech.

Preferably, the present technology includes a sensor such as a throat microphone that detects the vibration of the vocal cords, and a module that converts this vibration signal to a speech signal, e.g. a Boolean signal, indicating whether or not the patient is speaking or attempting to speak. This speech signal may be used by the breathing assistance system to conditionally modify its behaviour so as to facilitate or improve the quality of the patient's speech. Preferably, the behaviour modification takes the form of facilitating the flow of exhaled air to the atmosphere via the upper airway of the patient, thereby at least partially suppressing the upstream flow of exhaled air via the tracheostomy tube. At least a substantial portion of the exhaled air therefore flows via the upper airway of the patient, and in particular through his vocal cords, to facilitate or improve the quality of the patient's speech Once the patient has the breathing assistance system, particularly the sensor, according to the present technology in place, no more intervention is required from the patient in order to speak intelligibly. In particular, the present technology may improve the quality of speech among a category of patients, including those that are not able to actively interact with a system, e.g. by pressing a button. The speech resulting from the use of the present technology is more intelligible and thus increases the patients' quality of life without requiring any modification of behaviour by the patients.

One aspect of the present technology relates to provision of a minimum pressure of about 3 hPa below the vocal cords.

According to one aspect of the present technology, there is disclosed a breathing assistance system comprising: a ventilator, a breathing lumen arranged to communicate a flow of air between the ventilator and a tracheostomy tube in the trachea of a patient, and a sensor configured to generate a vibration signal representing vocal cord vibrations of the patient, wherein the system is configured to facilitate the flow of exhaled air to the atmosphere via the upper airway of the patient in response to detection in the vibration signal of speech or attempted speech by the patient.

According to one aspect of the present technology, there is disclosed a voice detection module configured to interact with a breathing assistance system, the module being adapted to: provide a vibration signal representing vocal cord vibrations of a patient whose ventilation is being supported by the breathing assistance system via a tracheostomy tube in the trachea of the patient; detect in the vibration signal speech or attempted speech by the patient; and in response to detection in the vibration signal of speech or attempted speech, modify the behaviour of the breathing assistance system so as to facilitate or improve the quality of the speech.

According to one aspect of the present technology, there is disclosed a method of facilitating or improving the quality of speech by a tracheostomised patient, the method comprising: supporting ventilation by the patient via a tracheostomy tube in the trachea of the patient, detecting speech or attempted speech by the patient, and facilitating the flow of exhaled air to the atmosphere via the upper airway of the patient in response to detection of speech or attempted speech by the patient.

Additional and/or alternative aspects relate to:

1. A breathing assisting system comprising: a ventilator, a tracheostomy tube for communicating between the ventilator and a trachea of a patient, and a sensor for monitoring vocal cord vibrations, wherein the system is adapted to at least partially suppress flow of expelled air via the tube in response to detection of vibration indicative of speech.

2. The system according to aspect 1 and comprising a valve in communication with the tube via which the expelled air can flow, and the at least partial suppression of flow of the expelled air via the tube comprises at least partially closing the valve.

3. The system according to aspects 1 or 2 and being adapted to urge the ventilator to apply positive pressure at the tube to at least contribute to the at least partial suppression of flow of the expelled air via the tube.

4. The system according to any one of the preceding aspects, wherein the sensor comprises a contact vibration sensor.

5. The system according to any one of the preceding aspects, wherein the sensor is throat microphone preferably to be attached externally to the throat of the patient.

6. The system according to aspects 4 or 5, wherein the sensor is sensitive only to vibrations generated by the patient in contact with the sensor.

7. The system according to anyone of the preceding aspects and being adapted to release the at least partial suppression to flow after cessation of detection of vocal cord vibrations indicative of speech.

8. The system according to aspect 7, wherein the release occurs after a given period of time has passed from the last detection of vocal cord vibrations indicative of speech.

9. The system according to aspect 8, wherein the given period of time is 1 second.

10. The system according to anyone of the preceding aspects and comprising means for receiving monitored signals from the sensor, and wherein a detection of vibration indicative of speech is determined by the means.

11. The system according to aspect 10, wherein the detection of vibration indicative of speech by the means is according to the vibration being within a range of 100 Hz to 3 kHz.

12. The system according to aspects 10 or 11, wherein the detection of vibration indicative of speech by the means is according to the vibration being detected present in a timed window of at least 200 ms.

13. The system according to aspects 10 or 11, wherein the detection of vibration indicative of speech by the means is according to the vibration occurring between 2 to 3 times in 500 ms.

14. The system according to aspect 2 and being adapted to support inspiration and exhalation breathing cycles of the patient, and wherein at least during an end of an inspiration cycle the valve is closed.

15. The system according to aspect 14, wherein during a given time window at a beginning of a subsequent exhalation cycle the valve is still closed.

16. A voice detection module for interacting with a breathing assisting system, the module being adapted to: receive monitored signals of vocal cord vibrations of a patient, detect from the monitored signals vibrations indicative of speech, and send a first communication to the breathing assisting system in response to detection of vibration indicative of speech.

17. The voice detection module of aspect 16 and being adapted to send a second communication to the breathing assisting system after ceasing to detect vibrations indicative of speech.

18. The voice detection module of aspect 17, wherein second communication is sent after a given period of time has passed from the last detection of vocal cord vibrations indicative of speech.

19. The voice detection module of aspect 18, wherein the given period of time is 1 second.

20. The voice detection module of anyone of aspects 16 to 19, wherein the detection of vibration indicative of speech is according to the vibration being within a range of 100 Hz to 3 kHz.

21. The voice detection module of anyone of aspects 16 to 20, wherein the detection of vibration indicative of speech is according to the vibration being detected present in a timed window of at least 200 ms.

22. The voice detection module of anyone of aspects 16 to 20 wherein the detection of vibration indicative of speech is according to the vibration occurring between 2 to 3 times in 500 ms.

23. A command module for interacting with: a voice detection module monitoring a patient, and a breathing assisting system of the type comprising a tracheostomy tube and an exhalation valve through which air exhaled via the tube from the patient can exit, the command module being adapted to: intercept commands communicated in the system towards the valve, receive signals from the voice detection module, and send a closing command to the valve if receiving a given signal that is indicative of speech even though an intercepted command at or prior to the given signal was an opening command.

24. A command module for interacting with: a voice detection module monitoring a patient, and a breathing assisting system comprising a tracheostomy tube, the command module being adapted to: intercept commands in the system aimed at affecting the flow via the tube, receive signals from the voice detection module, and in response to a given signal indicative of speech at least partially suppress the flow of expelled air via the tube from the patient even though an intercepted command at or prior to the given signal was to affect the flow differently.

Of course, portions of the aspects and/or claims may form sub-aspects of the present technology. Also, various ones of the claims, sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Breathing Assistance Systems

Figure 1:
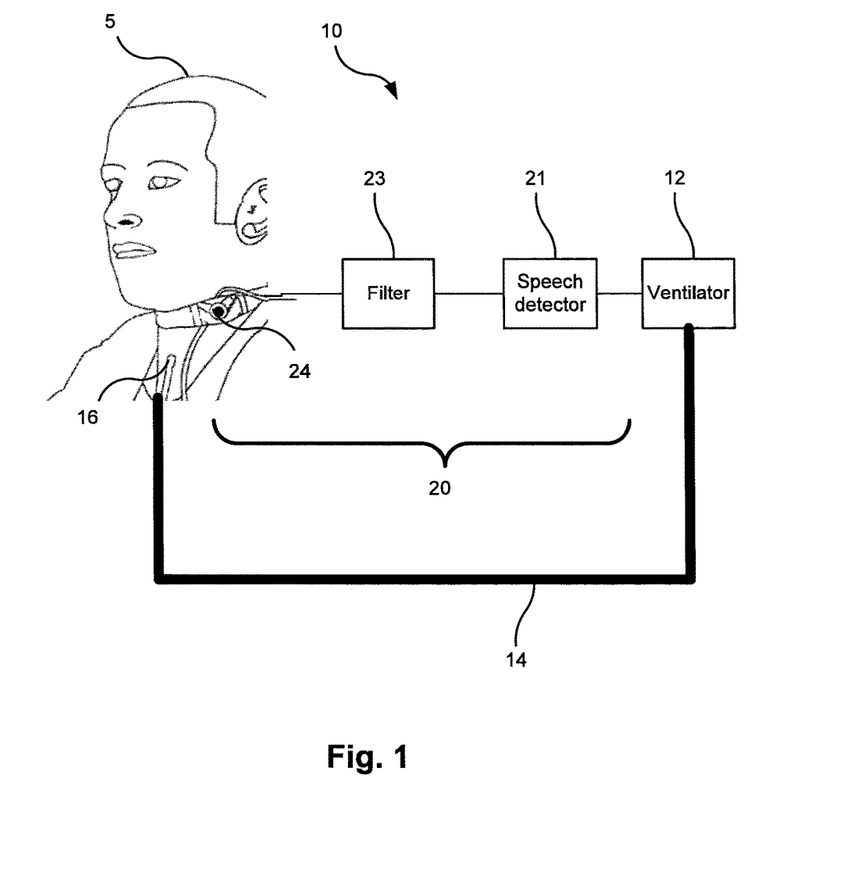
FIG. 1 shows general components of a breathing assistance system in accordance with one form of the present technology.
Figure 2:
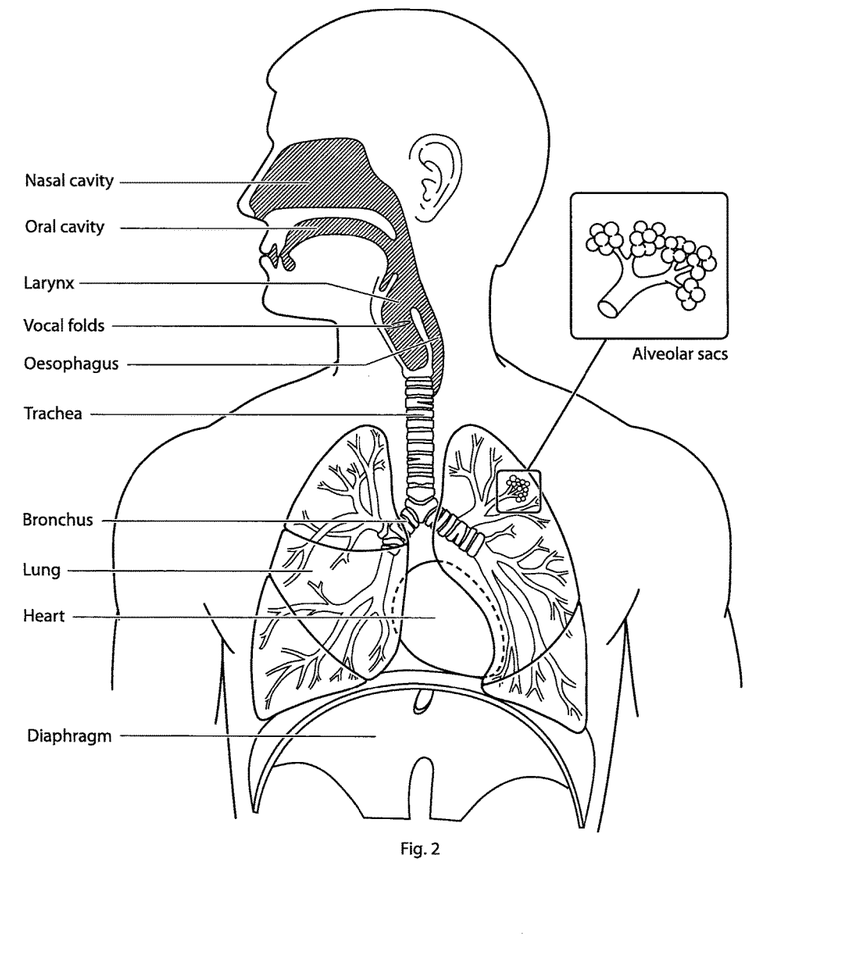
FIG. 2 shows an overview of a human respiratory system including the nasal and oral cavities, the larynx, vocal folds (vocal cords), oesophagus, trachea, bronchus, lung, alveolar sacs, heart and diaphragm.
Figure 3:
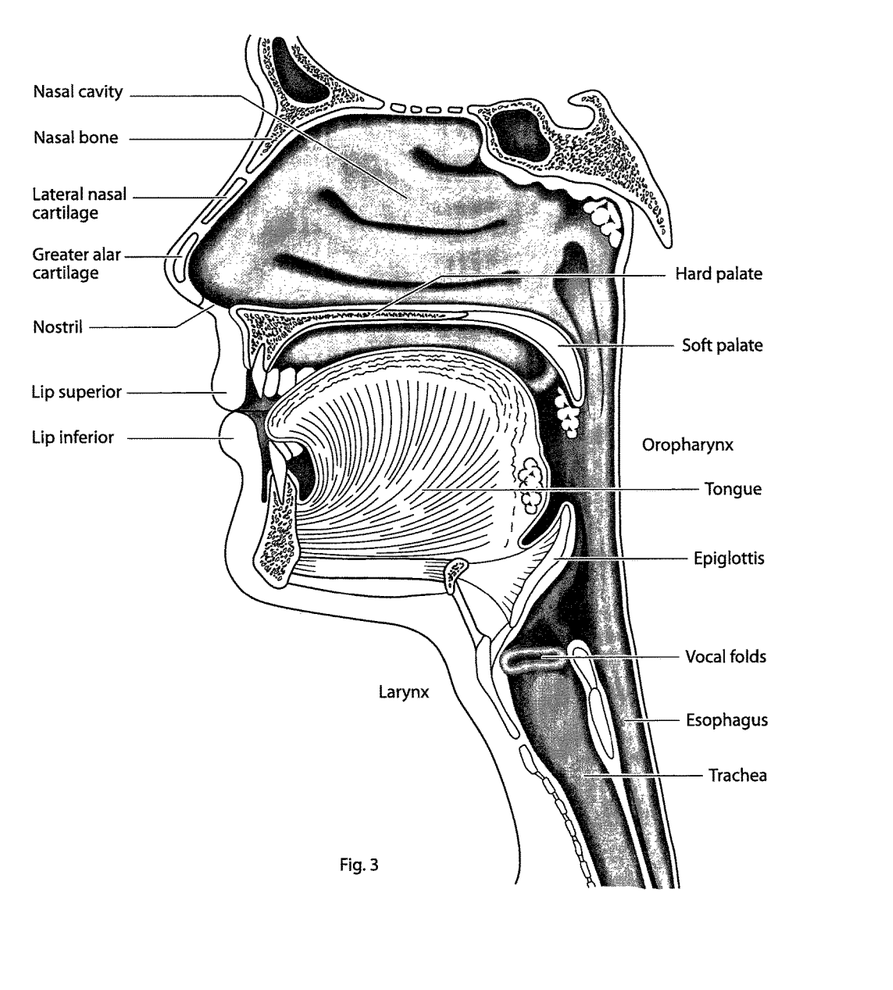
FIG. 3 shows a detailed view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

In one form, the present technology includes a breathing assistance system 10 for treating a respiratory disorder. The breathing assistance system 10 includes a ventilator 12 for supplying pressurised air or other breathable gas to a tracheostomised patient 5 via a breathing tube or lumen 14 connected to a tracheostomy tube 16 that is inserted into the trachea of the patient 5. The ventilator 12 is configured to support ventilation of the patient 5 by facilitating upstream and downstream flow of air via the tracheostomy tube 16 in synchrony with exhalation and inhalation portions respectively of breathing cycles of the patient 5.

A voice detection module 20 includes a sensor 24 that is configured to generate vibration signals representing vibrations in the vocal cords of the patient 5. The voice detection module 20 optionally includes a speech detector 21 and optionally includes a filter 23. The speech detector 21 detects speech or attempted speech in the generated vibration signals, after optional bandpass filtering by the filter 23 to limit the vibration signal to the audible frequency range, upon which the voice detection module 20 prompts the ventilator 12 to conditionally modify its behaviour in order to facilitate or improve the quality of the patient's speech.

The sensor 24 may be a contact vibration sensor. In one such implementation, the sensor 24 is a throat microphone attached externally to the throat of the patient 5. The sensor 24 may be made insensitive to any audible noise except the vibrations generated by the patient 5 in contact with the sensor 24.

The breathing assistance system 10 may therefore be seen to convert a vibration signal generated by the sensor 24 representing vibration of the vocal cords of the patient 5 to a speech signal indicating whether or not the patient is speaking or attempting to speak. The speech signal prompts the ventilator 12 to conditionally modify its behaviour in order to facilitate or improve the quality of the patient's speech. Such a breathing assistance system 10 may remove the need of the patient 5 to actively interact with the system 10 in order to speak intelligibly, and thus allow the ventilator 12 to have a safer/non-permanent behaviour or mode of operation that adjusts to the patient's respiratory needs.

In some embodiments of the breathing assistance system 10, the voice detection module 20 may be a part of the breathing assistance system 10. In other embodiments, the voice detection module 20 may function as a separate module, not forming part of the breathing assistance system 10 but rather being configured to interact with the breathing assistance system 10 or with a system similar to system 10.

Figure 4A:
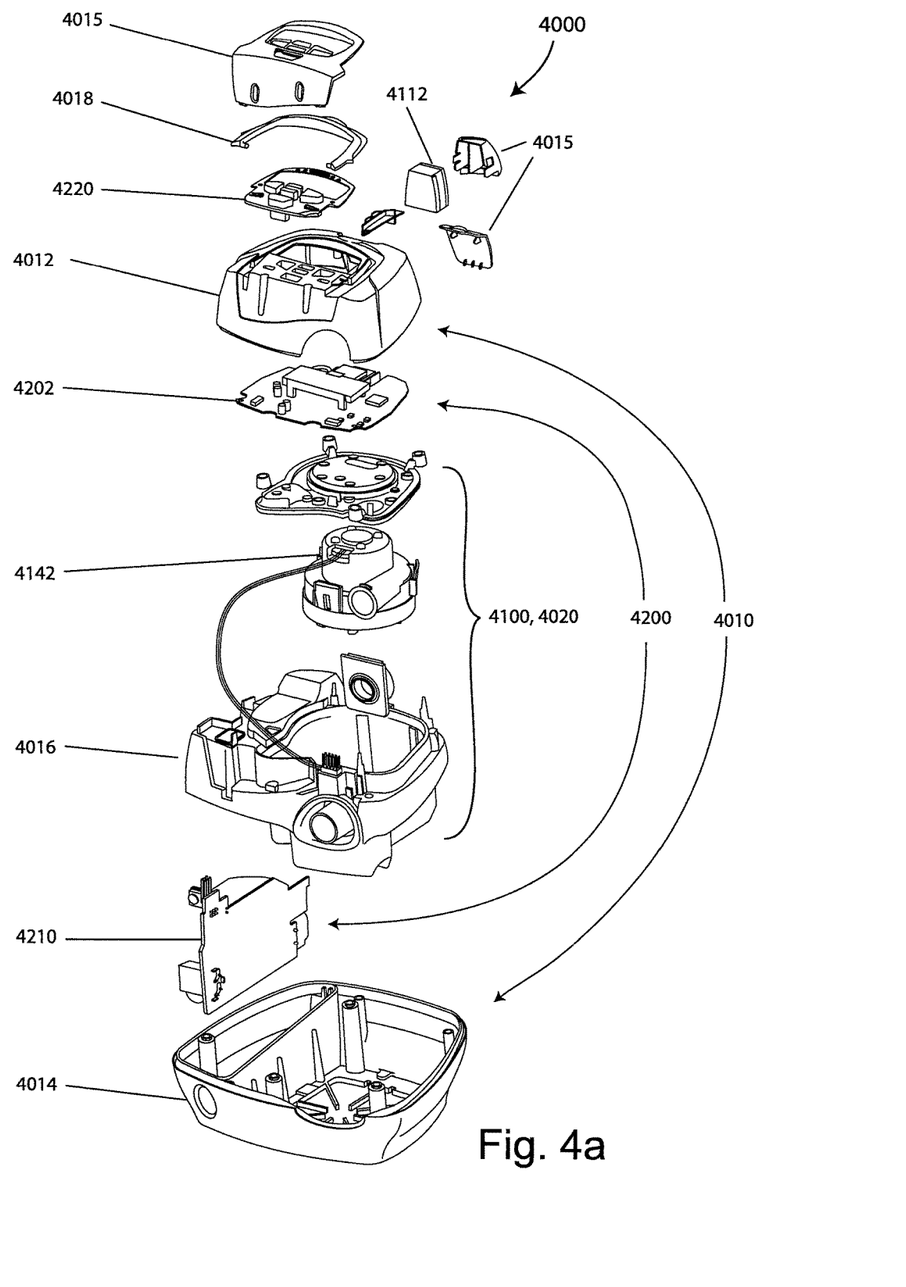
FIG. 4a shows a PAP device as used in a breathing assistance system such as in FIG. 1 in accordance with one form of the present technology.

A PAP device 4000 that may be used as the ventilator 12 in accordance with one aspect of the present technology comprises mechanical and pneumatic components 4100 and electrical components 4200. The PAP device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler 4122, a controllable pressure device 4140 capable of supplying air at positive pressure (preferably a blower 4142), and an outlet muffler 4124.

The preferred pneumatic block 4020 comprises a portion of the pneumatic path that is located within the external housing 4010.

Electrical components 4200 may be mounted on a single Printed Circuit Board Assembly (PCBA) 4202 including an electrical power supply 4210 and one or more input devices 4220. In an alternative form, the PAP device 4000 may include more than one PCBA 4202.

Figure 6:
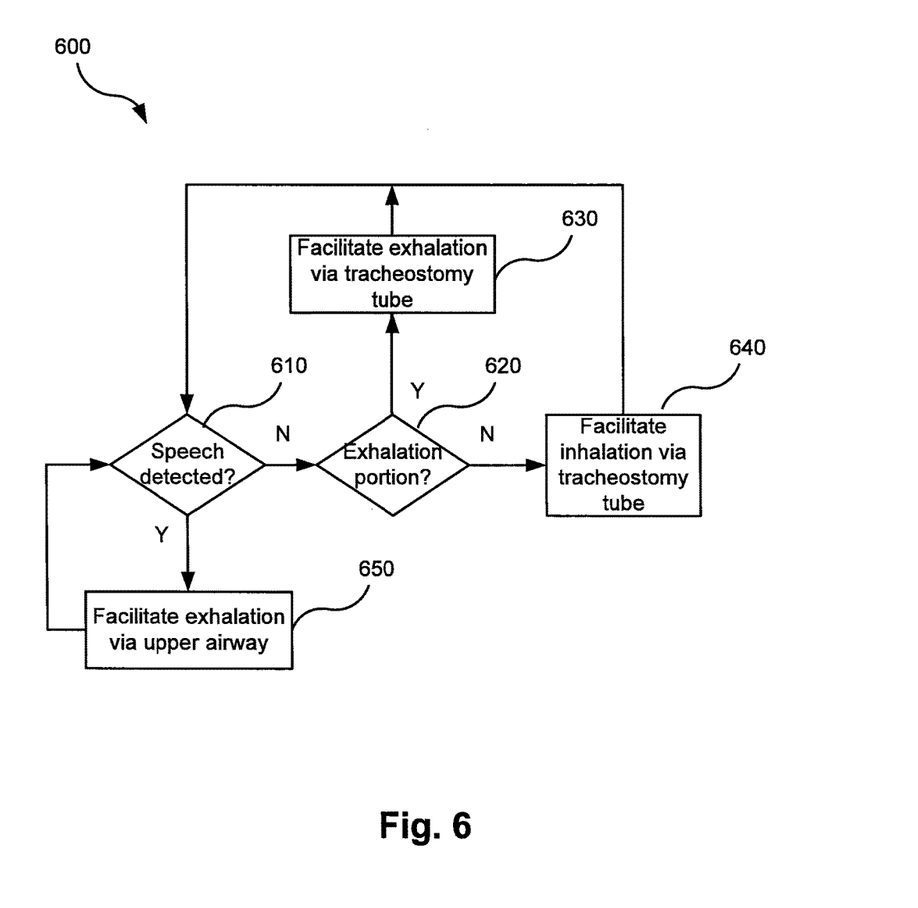
FIG. 6 is a flow chart illustrating a method of operation of a breathing assistance system such as in FIG. 1.

FIG. 6 is a flow chart illustrating a method 600 of operation of the breathing assistance system 10 according to one form of the present technology. The method 600 is in the form of a continuous loop.

In step 610, the voice detection module 20 determines whether the patient is speaking or attempting to speak. If no speech or attempted speech is detected by the voice detection module 20 ("N" at step 610), the ventilator 12 at step 620 determines in conventional fashion whether the patient 5 is within the exhalation portion of a breathing cycle. If so ("Y" at step 620), the ventilator 12 facilitates exhalation (upstream air flow) via the tracheostomy tube 16 (step 630). Otherwise, i.e. if the patient 5 is determined to be within the inhalation portion of a breathing cycle ("N" at step 620), the ventilator 12 facilitates inhalation (downstream air flow) via the tracheostomy tube 16 (step 640). After both steps 630 and 640, the method 600 returns to step 610.

Upon an affirmative detection of speech or attempted speech by the voice detection module 20 ("Y" at step 610), the voice detection module 20 may send out a first command via a wireless or wired primary channel 26 that prompts the breathing assistance system 10 to modify its behaviour so as to facilitate or improve the quality of the patient's speech. In one implementation, this may be achieved by facilitating exhalation via the upper airway of the patient 5 (step 650), e.g. by increasing the resistance to flow through the tracheostomy tube 16. This has the effect of at least partially suppressing the upstream flow of exhaled air via the tracheostomy tube 16. At least a substantial portion of the exhaled air therefore flows via the upper airway of the patient 5, and in particular through his vocal cords, to facilitate or improve the quality of the patient's speech. After step 650, the method 600 returns to step 610.

Once speech or attempted speech is no longer detected ("N" at step 610), or has not been detected for a predetermined period of time, if the ventilator 12 determines that the patient 5 is still within the exhalation portion of a breathing cycle ("Y" at step 620), the voice detection module 20 may send a second command via the primary channel 26 that prompts the ventilator 12 to cease the at least partial suppression of the upstream flow of exhaled air via the tracheostomy tube 16, and instead facilitate exhalation (upstream flow) via the tracheostomy tube 16 (step 630). Otherwise, i.e. if the patient 5 is determined to be within the inhalation portion of a new breathing cycle ("N" at step 620), the second command prompts the ventilator 12 to facilitate inhalation (downstream flow) via the tracheostomy tube 16 (step 640).

According to the operation of the breathing assistance system 10, as in for example the method 600, vibration signals generated by the sensor 24 are optionally filtered and then analysed by the voice detection module 20 to determine if the vibration signals are indicative of speech or an attempt at speech. A vibration signal that is indicative of speech may exhibit one or more of the following characteristics:

Quasi-periodic (sometimes called quasi-harmonic), denoting a waveform that is virtually periodic microscopically, but not necessarily periodic macroscopically, i.e. a waveform in which any one period is virtually identical to its adjacent periods but differing in frequency spectrum from periods much farther away in time (on the scale of a typical phoneme), and non-stationary (denoting that the quasi-periodic signal is limited in time), corresponding to voiced speech (e.g. voiced phonemes such as vowels).

Substantially within a range of audible frequencies (e.g. about 70 Hz to about 3 kHz), wherein preferably vibrations in the vocal cords have fundamental frequencies typically between about 80 Hz and about 300 Hz.

To be deemed indicative of speech, a vibration signal may be detected as a having one or more of the above characteristics throughout a single contiguous time window, of duration about 200 ms in one implementation, and/or multiple (e.g. two to three) times within an interval that is longer than the duration of the contiguous time window. In one implementation the interval is about 500 ms. In addition or alternatively, the speech detection could be performed using the voiced/unvoiced threshold determined in conventional linear prediction coding. Speech detection may also be performed using Voice Activity Detection techniques as used e.g. in conventional mobile telephone technologies.

Speech signals indicating speech or attempted speech may be generated all the time speech is detected, e.g. in accordance with the above criteria, and optionally also for a predetermined period Tg after the end of detection of speech, e.g. in accordance with the above criteria, particularly to take into account the pauses in, and unvoiced parts of, normal speech. At other times, speech signals indicating no speech or attempted speech may be generated. The period Tg may be configurable by a user of the system 10, or may be set to a fixed value, in one implementation equal to one second.

Figure 5A:
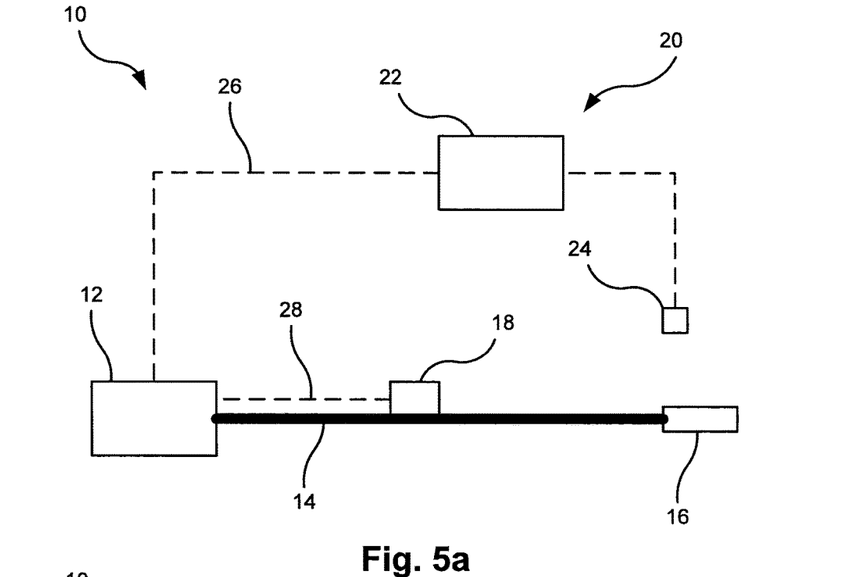
FIG. 5a shows a breathing assistance system such as in FIG. 1 in more detail in accordance with one embodiment of the present technology.
Figure 5B:
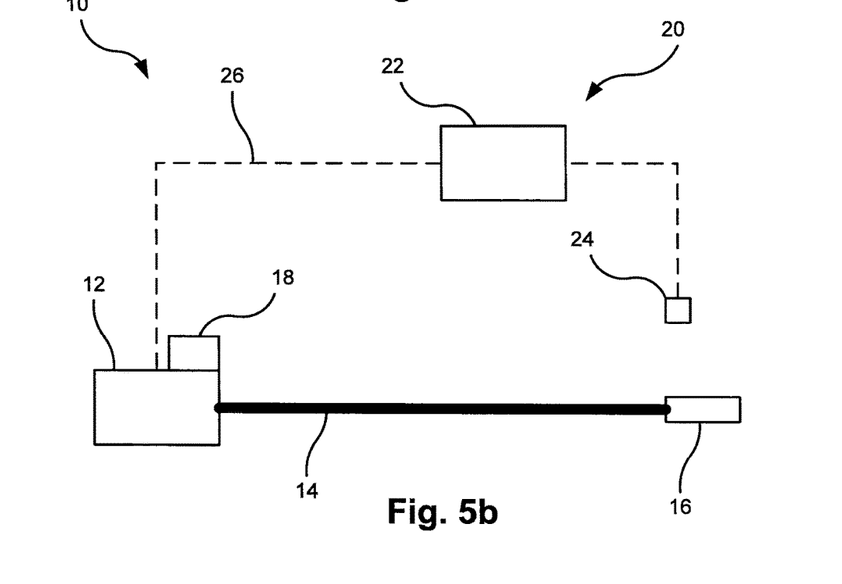
FIG. 5b shows a breathing assistance system such as in FIG. 1 in more detail in accordance with another embodiment of the present technology.

FIGS. 5a and 5b show two embodiments of a breathing assistance system 10 such as in FIG. 1. Absent any detected speech, the breathing assistance system 10 is adapted to support ventilation of the patient 5 by means of a valve 18 that can be urged between open and closed or substantially closed states in synchrony with exhalation and inhalation portions of the breathing cycle, in order to facilitate upstream and downstream flow of air in the tracheostomy tube 16 respectively as described above. In a variation, the valve 18 may be replaced by an active vent. The valve 18 may be in various locations in the breathing assistance system 10, preferably in locations that are in communication with the tracheostomy tube 16 or the air flow path to and from the tracheostomy tube 16. In the embodiment of FIG. 5a, the valve 18 is arranged in the air flow path on and/or in communication with the breathing lumen 14. In the embodiment of FIG. 5b, the valve 18 is arranged on and/or in communication with the ventilator 12, such as by being co-located with the ventilator 12.

In FIGS. 5a and 5b, the voice detection module 20 is provided with a control or base unit 22 in communication with the sensor 24. The control unit 22 may comprise the filter 23 and the speech detector 21 of the voice detection module 20 as illustrated in FIG. 1.

As described above in relation to the method 600, the ventilator 12 is configured to support ventilation of the patient 5 via the tracheostomy tube 16 by facilitating a flow of pressurised air downstream to the tracheostomy tube 16 via the breathing lumen 14 during the inhalation portion of each breathing cycle (step 640). To accomplish this, the ventilator 12 urges the valve 18 towards its closed or substantially closed state to seal or substantially seal the breathing lumen 14 so that all or substantially all the downstream air flows through the tracheostomy tube 16. During the exhalation portion of each breathing cycle, absent any detection of speech or attempted speech, the ventilator 12 urges the valve 18 towards its open state in order to facilitate an upstream flow of exhaled air from the exhaling patient 5 via the tracheostomy tube 16, the breathing lumen 14, and the valve 18 to the atmosphere (step 630).

If speech or attempted speech is detected by the voice detection module 20, the ventilator 12 urges the valve 18 towards its closed or substantially closed state to seal or substantially seal the breathing lumen 14 so that at least a substantial portion of the upstream flow is directed to the atmosphere via upper airway of the patient 5, to facilitate or improve the quality of the patient's speech (step 650).

Transmission of commands to urge the valve 18 towards its open or closed states may occur via a secondary wireless or wired channel 28 between the ventilator 12 and the valve 18. The secondary channel 28 is illustrated in the embodiment of FIG. 5a wherein the valve 18 is located on and/or in communication with the breathing lumen 14, but is not illustrated (although it may still be present) in the embodiment of FIG. 5b wherein the valve 18 is located on and/or in communication with the ventilator 12.

The primary channel 26 is illustrated in FIGS. 5a and 5b as leading to the ventilator 12. However, the primary channel 26 may lead from the voice detection module 20 to any other part of the system 10 or means associated with the system 10 which may be adapted to control the interaction between the various parts of the breathing assistance system 10 such as between the ventilator 12 and valve 18 as described above.

Figure 5C:
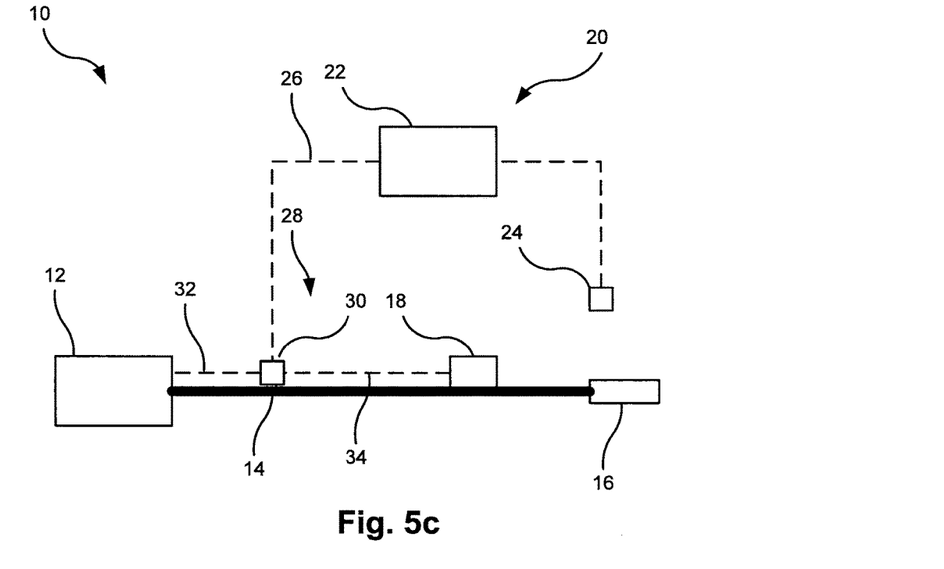
FIG. 5c shows a breathing assistance system such as in FIG. 1 in more detail in accordance with yet another embodiment of the present technology.

FIG. 5c illustrates a further embodiment of a breathing assistance system 10 containing a command module 30. The command module may alternatively function as a separate module that is not part of the breathing assistance system 10 but rather is configured to interact with the breathing assistance system 10 or with a system similar to the breathing assistance system 10. The command module 30 in the embodiment of FIG. 5c is located on/in the secondary channel 28, dividing it into first and second segments 32, 34 leading respectively to the ventilator 12 and the valve 18. The primary channel 26 in the embodiment of FIG. 5c enables communication between the voice detection module 20 and the command module 30 rather than between the voice detection module 20 and the ventilator 12, thus positioning the command module 30 as a hub or intersection point between the voice detection module 20, the ventilator 12, and the valve 18.

In the operation of the embodiment of FIG. 5c, commands communicated from the ventilator 12 towards the valve 18 along the first segment 32 of the secondary channel 28 may be intercepted at the command module 30, which is also configured to receive speech signals arriving over the primary channel 26 that indicate whether speech or an attempt at speech has been detected by the voice detection module 20. If the speech signal arriving at the command module 30 via the primary channel 26 indicates that the patient 5 is not attempting to speak, and a command from the ventilator 12 to urge the valve 18 towards its open state (as at step 630) has been intercepted, then the command module 30 may forward this intercepted command (or a command of equivalent effect) over the second segment 34 of the secondary channel 28 to the valve 18 so that the exhaled air flow from the patient 5 will continue to be facilitated via the tracheostomy tube 16. If the speech signal arriving at the command module 30 via the primary channel 26 indicates that the patient 5 is speaking or attempting to speak, and a command to urge the valve 18 towards its open state has been intercepted, then the following may occur. The command module 30 may transmit via the second segment 34 of the secondary channel 28 to the valve 18 a command that is different from the intercepted command. The effect of the transmitted command is to urge the valve 18 towards its closed state to partially suppress the upstream flow of exhaled air via the tracheostomy tube 16, which causes at least a substantial portion of the exhaled air to flow to the atmosphere via the upper airway of the patient 5, and in particular through his vocal cords, to facilitate or improve the quality of the patient's speech.

Figure 5D:
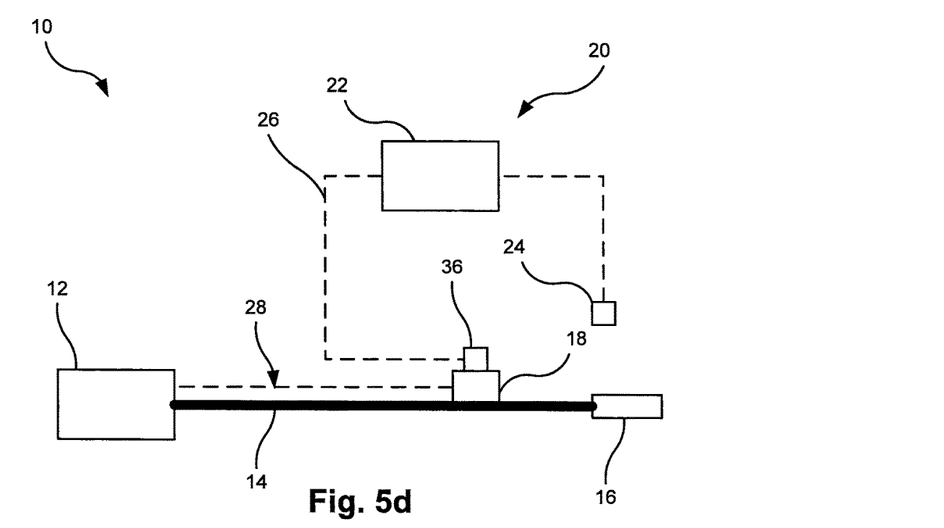
FIG. 5d shows a breathing assistance system such as in FIG. 1 in more detail in accordance with yet a further embodiment of the present technology.

In a yet further embodiment illustrated in FIG. 5d, the system 10 is provided with a secondary valve 36 that is located between the outlet of the valve 18 and the atmosphere. In a variation, the secondary valve 36 may be replaced by an active vent. The primary channel 26 in the embodiment of FIG. 5d may then enable communication between the control unit 22 and the secondary valve 36. In the operation of the embodiment of FIG. 5d, upon detection of speech or an attempt at speech by the voice detection module 20, a speech signal sent by the control unit 22 via the primary channel 26 and arriving at the secondary valve 36 instructs the secondary valve 36 to close or seal the outlet of the valve 18 (step 650). As a result, if a subsequent or previous command sent by the ventilator 12 via the secondary channel 28 urges the valve 18 towards its open state in order to permit exhaled air to be discharged to the atmosphere via the tracheostomy tube 16 (step 640), then due to the sealing of valve 18 by the secondary valve 36, the upstream flow of exhaled air via the tracheostomy tube 16 is at least partially suppressed. This causes at least a substantial portion of the exhaled air to flow via the upper airway of the patient 5, and in particular through his vocal cords, to facilitate or improve the quality of the patient's speech.

A voice detection module 20 including the secondary valve 36, as illustrated in the embodiment of FIG. 5d, may be particularly advantageous as an upgrade to or retrofitting of conventional breathing assistance systems that facilitates or improves the quality of speech of tracheostomised patients using the conventional breathing assistance systems.

Glossary

For the purposes of the present technology disclosure, in certain forms of the present technology, one or more of the following definitions may apply. In other forms of the present technology, alternative definitions may apply.

General

Air: In certain forms of the present technology, air supplied to a patient may be atmospheric air, and in other forms of the present technology atmospheric air may be supplemented with oxygen.

Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO$_2$), partial pressure of carbon dioxide (PCO$_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Positive Airway Pressure (PAP) device: A device for providing a supply of air at positive pressure to the airway of a patient.

Aspects of the Respiratory Cycle

Effort (breathing): Preferably breathing effort will be said to be the work done by a spontaneously breathing person attempting to breathe.

Expiratory (exhalatory) portion of a breathing cycle: The period from the start of expiratory flow to the start of inspiratory flow.

Inspiratory (inhalatory) portion of a breathing cycle: Preferably the period from the start of inspiratory flow to the start of expiratory flow will be taken to be the inspiratory portion of a breathing cycle.

Positive End-Expiratory Pressure (PEEP): The pressure above atmosphere in the lungs that exists at the end of expiration.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in liters per minute.

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$.

Terms for Ventilators

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Ventilator: A mechanical device that provides pressure support to a patient to perform some or all of the work of breathing.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilised to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilised, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognise that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

Reference Signs List
10 breathing assistance system
12 ventilator
14 breathing lumen
16 tracheostomy tube
18 valve
20 voice detection module
21 speech detector
22 control unit
23 filter
24 sensor
26 primary channel
28 secondary channel
30 command module
32 first segment
34 second segment
36 secondary valve
600 method
610 step
620 step
630 step
640 step
650 step
4000 pap device
4010 external housing
4012 upper portion
4014 portion
4015 panel
4016 chassis
4018 handle
4020 pneumatic block
4100 pneumatic component
4112 inlet air filter
4122 inlet muffler
4124 outlet muffler
4140 controllable pressure device
4142 blower
4200 electrical component
4202 PCBA
4210 electrical power supply
4220 input device

The invention claimed is:

1. A breathing assistance system comprising:
a ventilator,
a breathing lumen connectable to a tracheostomy tube in the trachea of a patient and arranged to communicate a flow of air between the ventilator and the tracheostomy tube,
a primary valve in communication with the tracheostomy tube, the primary valve being configured to move toward an open position during an exhalation portion of a breathing cycle of the patient and toward a closed position during an inhalation portion of the breathing cycle of the patient,
a secondary valve located between an outlet of the primary valve and the atmosphere, and
a sensor configured to generate a vibration signal representing vocal cord vibrations of the patient,
wherein the system is configured to reduce an amount of air exhaled through the tracheostomy tube by urging the secondary valve toward its closed state to increase a flow of exhaled air to the atmosphere via the upper airway of the patient in response to a detection in the vibration signal of attempted speech by the patient.

2. The system according to claim 1, configured to increase the flow of exhaled air to the atmosphere via the upper airway of the patient by setting a positive end-expiratory pressure to a value that is larger than a normal value.

3. The system according to claim 1, wherein the primary valve is in communication with the breathing lumen.

4. The system according to claim 1, wherein the primary valve is co-located with the ventilator.

5. The system according to claim 1, wherein the sensor comprises a contact vibration sensor in contact with the patient.

6. The system according to claim 5, wherein the sensor is a throat microphone attached externally to a throat of the patient.

7. The system according to claim 5, wherein the sensor is insensitive to audible noise other than vibrations generated by the patient.

8. The system according to claim 1, being further configured to cease the increase of the flow of exhaled air to the atmosphere via the upper airway of the patient after an end of detection in the vibration signal of attempted speech by the patient.

9. The system according to claim 8, configured to cease the increase of the flow of exhaled air to the atmosphere via the upper airway of the patient a predetermined period after the end of the detection of attempted speech.

10. The system according to claim 9, wherein the predetermined period has a duration of one second.

11. The system according to claim 1, wherein the detection of attempted speech in the vibration signal is performed by a voice detection module.

12. The system according to claim 11, wherein the voice detection module comprises a filter.

13. The system according to claim 11, wherein the increasing is performed by a command module in communication with the voice detection module.

14. The system according to claim 1, wherein the detection of attempted speech in the vibration signal occurs when the vibration signal exhibits one or more of the group of characteristics consisting of:
quasi-periodic and non-stationary; and
within a range of audible frequencies.

15. The system according to claim 14, wherein the detection of attempted speech in the vibration signal occurs when the vibration signal exhibits one or more of the group of characteristics throughout a contiguous time window having a duration of about 200 ms.

16. The system according to claim 14, wherein the detection of attempted speech in the vibration signal occurs when the signal exhibits one or more of the group of characteristics multiple times within an interval having a duration of about 500 MS.

17. A voice detection module configured to interact with a breathing assistance system having a primary valve and a secondary valve, the primary valve being in communication with a tracheostomy tube, the primary valve being adapted to move toward an open position during an exhalation portion of a breathing cycle of a patient and to move toward a closed position during an inhalation portion of the breathing cycle of the patient, the secondary valve being located between an outlet of the primary valve and the atmosphere, the module being adapted to:
provide a vibration signal representing vocal cord vibrations of the patient whose ventilation is being supported by the breathing assistance system via the tracheostomy tube in the trachea of the patient;
detect in the vibration signal attempted speech by the patient; and
in response to the detection in the vibration signal of attempted speech, provide a control signal configured to modify a behaviour of the breathing assistance system so as to facilitate or improve a quality of speech, wherein the modifying comprises, reducing an amount of air exhaled through the tracheostomy tube by urging the secondary valve toward its closed state, thereby increasing a flow of exhaled air via the upper airway of the patient.

18. The voice detection module according to claim 17, wherein the increasing of the flow of exhaled air via the upper airway is to the atmosphere.

19. The voice detection module of claim 17, configured to modify the behaviour of the breathing assistance system for a predetermined period after an end of detection of attempted speech.

20. The voice detection module of claim 19, wherein the predetermined period is one second in duration.

21. The voice detection module of claim 17, wherein the detection of attempted speech occurs when the vibration signal exhibits one or more of the group of characteristics consisting of:
quasi-periodic and non-stationary; and
within a range of audible frequencies.

22. The voice detection module of claim 21, wherein the detection of attempted speech occurs when the vibration signal exhibits one or more of the group of characteristics throughout a contiguous time window having a duration of about 200 ms.

23. The voice detection module of claim 21, wherein the detection of attempted speech occurs when the vibration signal exhibits one or more of the group of characteristics multiple times within an interval having a duration of about 500 ms.

24. The voice detection module of claim 17, comprising a sensor configured to generate the vibration signal representing vocal cord vibrations of a patient.

25. The voice detection module according to claim 24, wherein the sensor comprises a contact vibration sensor in contact with the patient.

26. The voice detection module according to claim 25, wherein the sensor is a throat microphone attached externally to the throat of the patient.

27. The voice detection module according to claim 25, wherein the sensor is insensitive to audible noise other than vibrations generated by the patient.

28. A method of facilitating or improving a quality of speech by a tracheostomised patient, the method comprising:
supporting ventilation by the patient via a tracheostomy tube in the trachea of the patient by urging a primary valve toward an open position during an exhalation portion of a breathing cycle of the patient and by urging the primary valve toward a closed position during an inhalation portion of the breathing cycle of the patient, the primary valve being in communication with the tracheostomy tube,
detecting attempted speech by the patient, and
reducing an amount of air exhaled through the tracheostomy tube by urging a secondary valve located between an outlet of the primary valve and the atmosphere toward its closed state, thereby increasing a flow of exhaled air to the atmosphere via the upper airway of the patient in response to the detection of attempted speech by the patient.

29. The method according to claim 28, wherein the increasing the flow of exhaled air to the atmosphere via the upper airway of the patient comprises setting a positive end-expiratory pressure to a value that is larger than a normal value.

30. The method according to claim 28, wherein the increasing the flow of exhaled air to the atmosphere via the upper airway of the patient comprises urging the secondary valve toward its closed state, the secondary valve being in communication with a lumen connected to the tracheostomy tube, the primary valve being attached to the lumen.

31. The method according to claim 28, wherein the urging the secondary valve toward its closed state further comprises sealing the outlet of the primary valve, the primary valve being located along a lumen connected to the tracheostomy tube.

32. The method according to claim 28, wherein the detecting attempted speech by the patient is via a contact vibration sensor attached externally to a throat of the patient.

33. The method according to claim 28, further comprising ceasing the increasing of the flow of exhaled air to the atmosphere via the upper airway of the patient after an end of detection of speech or attempted speech by the patient.

34. The method according to claim 33, wherein the ceasing occurs a predetermined period after the end of detection of attempted speech.

35. The method according to claim 34, wherein the predetermined period has a duration of one second.

36. The method according to claim 28, wherein the detection of attempted speech comprises analysing a vibration signal representing vocal cord vibrations of the patient to detect one or more of the group of characteristics consisting of:
quasi-periodic and non-stationary; and
within a range of audible frequencies.

37. The method according to claim 36, wherein the detection of attempted speech occurs when the vibration signal exhibits one or more of the group of characteristics throughout a contiguous time window having a duration of about 200 ms.

38. The method according to claim 36, wherein the detection of attempted speech in the vibration signal occurs when the vibration signal exhibits one or more of the group of characteristics multiple times within an interval having a duration of about 500 ms.

\* \* \* \* \*